US005292757A

United States Patent [19]

Ohsumi et al.

[11] Patent Number: 5,292,757

[45] Date of Patent: Mar. 8, 1994

[54] 1,4-DIHYDROPYRIDINE COMPOUNDS USEFUL AS REVERSE RESISTANCE AGENTS

[75] Inventors: Koji Ohsumi; Takaaki Sekiyama; Ryusuke Nakagawa; Takashi Tsuji; Yoshihiro Morinaga; Kazuo Ohishi, all of Tokyo, Japan

[73] Assignee: Ajinomoto Company, Inc., Tokyo, Japan

[21] Appl. No.: 873,159

[22] Filed: Apr. 24, 1992

[30] Foreign Application Priority Data

Apr. 26, 1991 [JP] Japan .................................. 3-191362

[51] Int. Cl.[5] .................... C07D 211/90; A61K 31/44

[52] U.S. Cl. ................................ 514/332; 514/231.5; 514/255; 514/318; 514/356; 544/124; 544/360; 546/193; 546/263; 546/316

[58] Field of Search ....................... 546/263, 316, 193; 514/332, 356, 231.5, 255, 318; 544/124, 360

[56] References Cited

FOREIGN PATENT DOCUMENTS

| | | | |
|---|---|---|---|
| 0123850 | 11/1984 | European Pat. Off. | 546/273 |
| 0197488 | 10/1986 | European Pat. Off. | 546/273 |
| 0330470 | 8/1989 | European Pat. Off. | 546/273 |
| 0353692 | 2/1990 | European Pat. Off. | 546/273 |
| 8809331 | 12/1988 | PCT Int'l Appl. | 546/273 |
| 9109846 | 7/1991 | PCT Int'l Appl. | 546/273 |

OTHER PUBLICATIONS

Chemical Abstracts, vol. 112, No. 17, Abstract No. 158,059s, p. 200, Apr. 23, 1990.

*Primary Examiner*—C. Warren Ivy
*Assistant Examiner*—Zinna N. Davis
*Attorney, Agent, or Firm*—Sughrue, Mion, Zinn, Macpeak & Seas

[57] ABSTRACT

1,4-dihydropyridine derivatives of Formula 1 or pharmaceutically acceptable salts thereof:

Formula 1

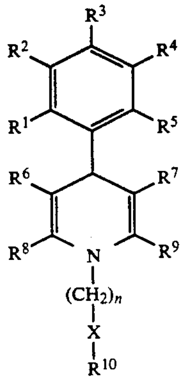

wherein the substituents are disclosed herein and which are useful against tumor cells which have acquired resistance to one or more drugs used as chemotherapeutic agents.

9 Claims, No Drawings

1,4-DIHYDROPYRIDINE COMPOUNDS USEFUL AS REVERSE RESISTANCE AGENTS

BACKGROUND OF THE INVENTION

1. Field of the Invention

The present invention relates to 1,4-dihydropyridine derivatives and their use against tumour cells which have acquired resistance to one or more drugs being used as chemotherapeutic agents.

Where chemotherapy is used to treat cancers, the anti-cancer agent being administered, frequently becomes ineffective during treatment, a phenomenon known as 'acquired drug resistance'. In some cases this resistance can be to several kinds of anti-cancer agents i.e. a 'multidrug resistance'.

It has been shown that the tumour cells which have acquired this multidrug resistance show enhanced excretion of the anti-cancer agents which are being administered as a treatment for the cancer. (T. Tsuruo, Pharmacia Review, No. 23, 115-125 (1987) and Japanese Journal of Cancer Research 79, 285-296 (1988)).

It is not practicable to overcome this problem by simply administering larger doses of the anti-cancer agent(s) as these agents have severe side-effects. Animal tests have suggested that the problem may be overcome by administering the anti-cancer agent(s) in combination with a calcium antagonist, (T. Tsuruo, Pharmacia Review, No. 23, 115-125 (1987)). However, the use of calcium antagonists has not provided a practicable solution to the problem, as the amounts of calcium needed are highly toxic and cause a lowering of blood pressure. Thus, there is a need for therapeutic agents which may help overcome the problems of acquired drug resistance.

Japanese Patent Application Laid Open No. 1-316357 discloses that 1-substituted 1,4-dihydropyridine derivatives may be useful as drugs for overcoming acquired resistance to anti-cancer agents. A series of compounds are disclosed which are free of calcium antagonizing action. However, the compounds are extremely hydrophobic so that their administration would present practical difficulties. The application does not test the effectiveness of the compounds in vivo.

There is a need for drugs useful for overcoming multi-drug resistance but which exhibit low toxicity.

SUMMARY OF THE INVENTION

According to a first aspect of the present invention there is provided a compound of formula 1:

Formula 1

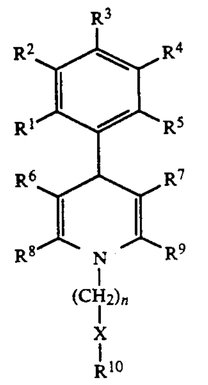

wherein each of $R^1$,$R^2$,$R^3$,$R^4$ and $R^5$ independently represents a hydrogen atom, a lower alkyl group having 1 to 3 carbon atoms such as methyl or ethyl, a hydroxy group, a lower alkyloxy group having 1 to 3 carbon atoms, such as methoxy or ethoxy, or a nitro group, or two substituents adjacent to each other on the benzene ring are combined together to form an alkylenedioxy group having 1 to 3 carbon atoms.

At least one of $R^6$ and $R^7$ represents an alkyloxycarbonyl group or an alkylaminocarbonyl group in which the alkyl moiety has a nitrogen-containg substituent. Where only one of $R^6$ and $R^7$ represents such a group, the other is an alkyloxycarbonyl group.

For example, $R^6$ and $R^7$ may represent any one of a pyridylalkyloxycarbonyl group or a pyridylalkylaminocarbonyl group, which may be substituted on the pyridyl moiety, an N,N-dialkylaminoalkyloxycarbonyl group, an (N,N-dialkylamino)-alkylaminocarbonyl group, an N,N-alkylarylaminoalkyloxycarbonyl group, an (N,N-alkylarylamino)alkylaminocarbonyl group, an N,N-diaralkylaminoalkyloxycarbonyl group, an (N,N-diaralkylamino)alkylaminocarbonyl group, an N,N-aralkylalkylaminoalkyloxycarbonyl group and an (N,N-aralkylalkylamino)alkylaminocarbyl group, wherein two substituents present adjacent to each other on the nitrogen atom in the nitrogen-containing substituent may take a cyclic structure. Specific examples include an N-alkylpiperazinoalkyloxycarbonyl group, an N-arylpiperazinoalkyloxycarbonyl group, an N-aralkylpiperazino-alkyloxycarbonyl group, an (N-alkylpiperazinoalkyl)amino-carbonyl group, an (N-arylpiperazinoalkyl)aminocarbonyl group, an (N-aralkylpiperazinoalkyl)aminocarbonyl group, a morpholinoalkylaminocarbonyl group, a morpholinoalkyloxycarbonyl group, a piperidinoalkyloxycarbonyl group, a piperidinoalkylaminocarbonyl group, a pyrrolidinoalkyloxycarbonyl group, a pyrrolidinoalkylaminocarbonyl group, etc.

Each of $R^8$ and $R^9$ independently represents a hydrogen atom or a lower alkyl group having 1 to 5 carbon atoms such as methyl or ethyl.

n represents an integer of 2 to 9

X represents a methylene group or an oxygen atom, wherein the methylene may have thereon a lower alkyl group having 1 to 5 carbon atoms, a hydroxy group or a lower alkyloxy group having 1 to 5 carbon atoms.

$R^{10}$ represents an aryl group or an aralkyl group, wherein the aryl moiety in the aryl group and aralkyl group may have a substituent selected from the group consisting of a halogen atom, such as fluoride, chloride, bromide, or iodide, a lower alkyl group having 1 to 5 carbon atoms, such as methyl or ethyl, a lower alkyloxygroup having 1 to 5 carbon atoms, a hydroxy group an aryl group, such an phenyl, an aryloxy group such as phenoxy, an aralkyl group such as benzyl, an aralkyloxy group such as benzyloxy, nitro group, amino group, or two substituents adjacent to each other on the benzene ring are combined together to form an alkylenedioxy group having 1 to 3 carbon atoms.

Examples of the aryl group $R^{10}$ include phenyl, naphthyl, pyridyl, quinolyl, isoquinolyl, etc. and examples of the aryl moiety in the aralkyl group include phenyl, naphthyl, pyridyl, quinolyl, isoquinolyl, etc. Examples of aralkyl group including these aryl moieties, include benzyl, naphthylmethyl, pyridylmethyl, quinolylmethyl, isoquinolylmethyl, etc.

Japanese Patent Application Laid Open No. 1-316357 discloses that 1-substituted 1,4-dihydropyridine derivatives are useful as agents for overcoming acquired resistance to cancer treatment drugs but there is no description of derivatives having an amide or ester containing nitrogen atom in the alkyl moiety as a substituent at the 3- or 5-position.

According to other aspects of the invention there are provided; a pharmaceutical composition containing an effective amount of a compound of formula 1 or a salt thereof together with a pharmaceutically acceptable excipient, diluent or carrier; a pharmaceutical product containing an effective amount of a compound of formula 1 or a pharmaceutically acceptable salt thereof and an anti-cancer drug as a combined preparation for simultaneous, separate, or sequential use in cancer therapy; a pharmaceutical product which is a composition comprising effective amounts of both of a compound of formula 1, or a pharmaceutically acceptable salt thereof, and of an anti-cancer drug; and a method of treatment of the human or animal patient to prevent or reduce acquired resistance to anti-cancer agents comprising administration of an effective amount of a compound of formula 1 or a salt thereof to the patient.

DETAILED DESCRIPTION OF THE INVENTION

Preferred derivatives of formula 1 are those 1,4-dihydropyridine derivatives wherein at least one of $R^6$ and $R^7$ is a group as represented by formula 2, or formula 3 below.

Formula 2

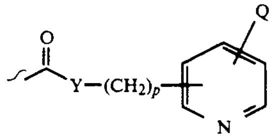

Formula 3

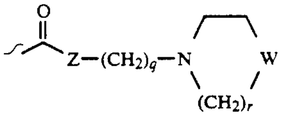

Some of these compounds have been shown to possess a high activity and to be effective in an animal model at improving the prolongation of life which may be achieved by the use of carcinostatic agents.

In formulae 2 and 3, Y represents an oxygen atom or NH; Q represents a hydrogen atom, a halogen atom, an alkyl group such as methyl, ethyl, isopropyl, etc.; an aryl group such as phenyl, pyridyl, etc; an aralkyl group such as benzyl, etc ; or a lower aryloxy group having 1 to 5 carbon atoms, p represents an integer of 1 to 4. Z represents an oxygen atom or NH; W represents a methylene group, nitrogen atom or oxygen atom, wherein the methylene group is optionally substituted with an alkyl group having 1 to 5 carbon atoms, an aryl group, an aralkyl group or carbonyl group; and the nitrogen atom is optionally substituted with an alkyl group having 1 to 5 carbon atoms such as methyl, ethyl, isopropyl, etc.; an aryl group such as phenyl, pyridyl, etc., an aralkyl group such as benzyl, diphenylmethyl, etc., or a carbonyl group such as an alkoxycarbonyl group. q represents an integer of 1 to 4. r represents an integer of 1 to 3.

According to a second aspect of the invention a method is provided for the production of derivatives of the first aspect.

The derivatives may, for example be prepared by a condensation reaction in which a compound of formula 1a or 1b, or a corresponding activated acid derivative, is reacted with a compound of formula $R^{13}$—OH or $R^{14}$—$NH_2$.

1a

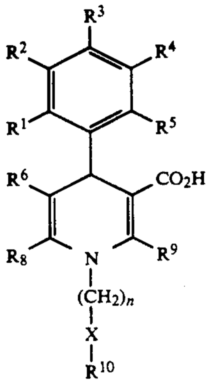

1b

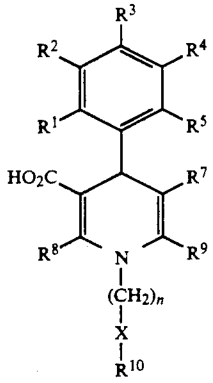

$R^1$ to $R^{10}$, X and n are as defined above. Each of $R^{13}$ and $R^{14}$ represents an alkyl group having a nitrogen containing substituent. The acid gorup may be activated as, for example, an acid halide, acid anhydride, ester or imidazolide.

One possible complete scheme for producing derivatives of formula 1 is indicated below in Scheme I. Scheme II shows one particular example of the general Scheme I.

SCHEME I

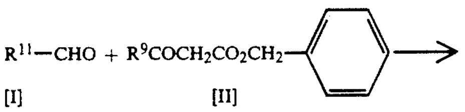

[I] [II]

-continued
SCHEME I
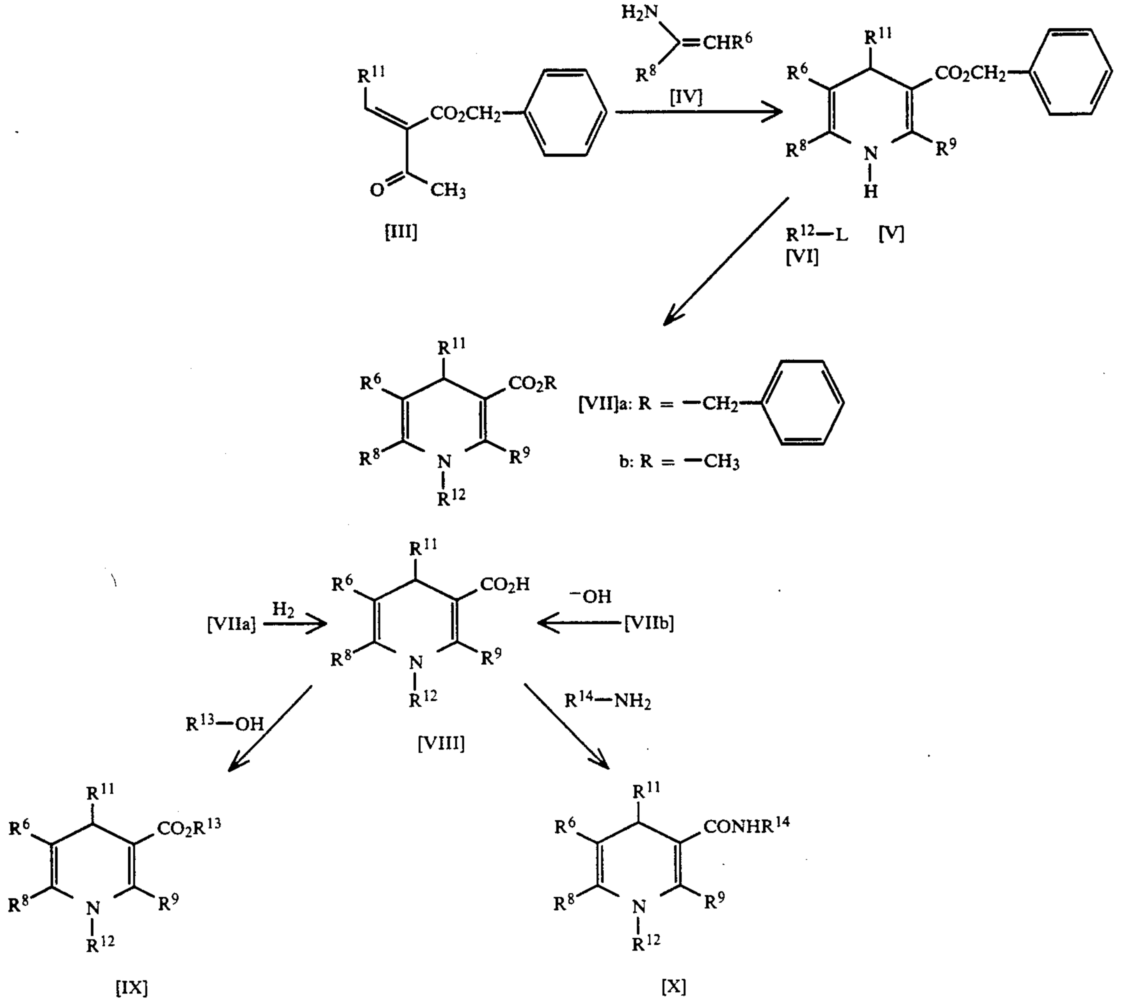
SCHEME II
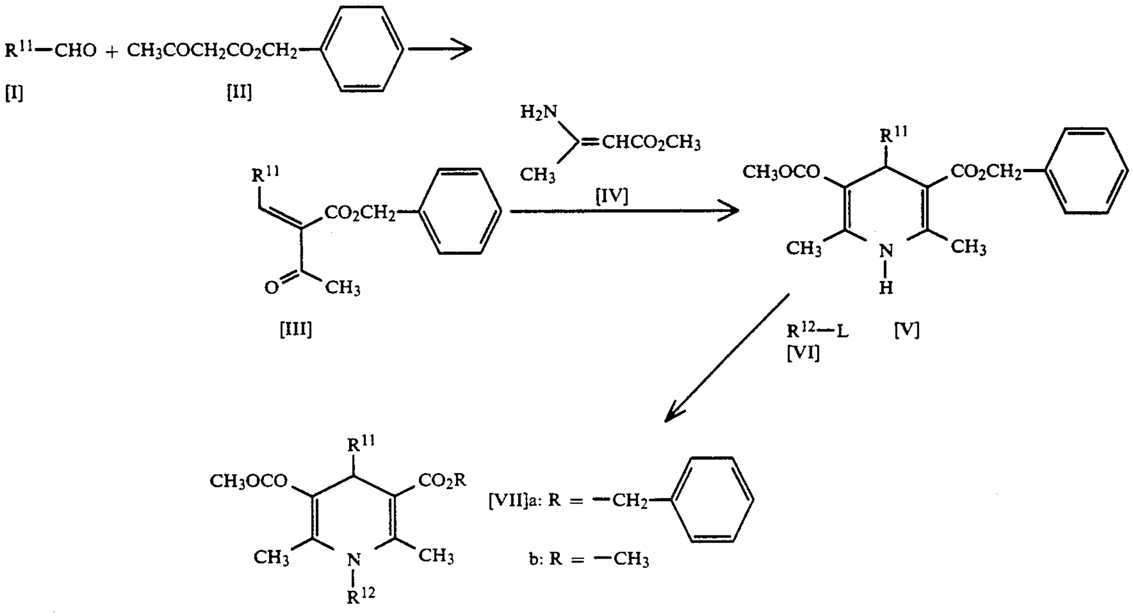

-continued

SCHEME II

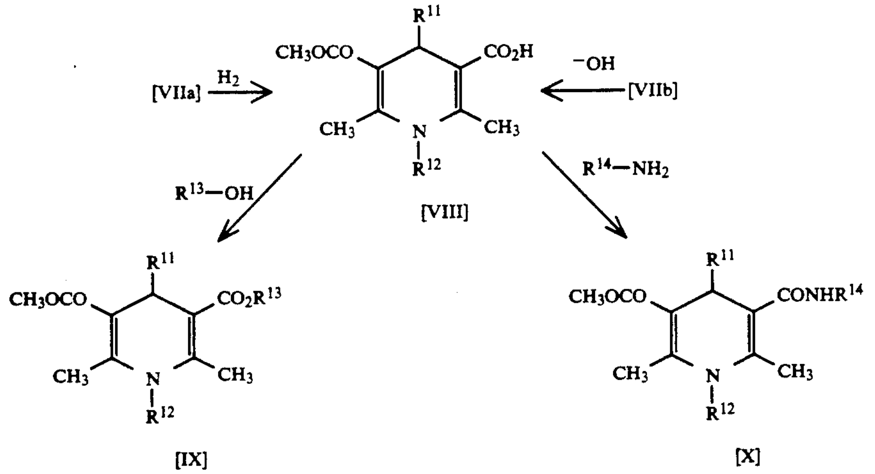

According to scheme II, compound [III], obtained by dehydrative condensation of aromatic aldehyde [I] with benzyl acetoacetate [II], and methyl 3-aminocrotonate [IV] are heated to reflux in the presence or in the absence of an organic solvent. The thus obtained asymmetric dihydropyridine derivative [V] is further reacted with the compound represented by general formula [VI] in an organic solvent inert to the reaction, e.g., dioxane, dimethylformamide, dimethylsulfoxide, etc., in the presence of a base such as sodium hydride or potassium *t*-butoxide, etc. to give 1-substituted 1,4-dihydropyridine [VIIa] ($R=CH_2Ph$). [VIIa] is subjected to catalytic hydrogenation using palladium/carbon as a catalyst in a hydrogen atmosphere to convert it into the carboxylic acid [VIII] followed by dehydrative condensation with the alcohol or the amine to give the ester [IX] or the amide [X] respectively. The carboxylic acid [VIII] may also be obtained by alkali hydrolysis of symmetric 1-substituted 1,4-dihydropyridine-3,5-dicarboxylic acid dimethylester [VIIb] ($R=CH_3$).

L represents a leaving group such as halogen, *p*-toluenesulfonate, etc. which is conventional in organic synthetic chemistry. Each of $R^{11}$ and $R^{12}$ represents a substituent at the 4- or 1-position of the dihydropyridine ring in formula 1; each of $R^{13}$ and $R^{14}$ represents an alcohol or amine moiety wherein substitutent $R^6$ or $R^7$ at the 3- or 5-position in formula 1 is an ester or an amide. Compounds of formula 1 wherein each of $R^6$ and $R^7$ contain a nitrogen-containing alkyl group may be produced by appropriate treatment of a compound having only one such group. For example a compound as [XI] or [X] in scheme II could be deesterified and subsequently esterfied or amidated with an alcohol or amine having a nitrogen-containing alkyl group.

Preferred compounds of the first aspect of the invention are derivatives of formula I in optically active form. Optically active derivatives may be prepared by resolution of a mixture of stereoisomers of formula I. Preferably, optically active ester [XI] or amide [X] can be prepared by esterification or amidation of the optically active carboxylic acid [VIII] which is prepared by resolution of a salt of racemic carboxylic acid and an optically active amine such as (−) cinchonidine by crystallisation.

The reaction product formed by the process described above, namely, the compound represented by formula 1 can be easily isolated and purified from the reaction mixture by conventional methods for isolation and purification, for example, extraction with a solvent, chromatography, crystallization, etc.

Pharmaceutically acceptable salts of the derivatives of the present invention may be prepared by protonation of compounds of formula 1 with a suitable acid. The hydrochloride salt may, for example, be prepared by the use of hydrochloric acid.

The 1,4-dihydropyridine derivatives of the present invention possess a remarkable activity for overcoming resistance to anti-cancer drugs as compared to the compounds disclosed in Japanese Patent Application No 1-316357. The 1,4-dihydropyridine derivatives are thought to prevent excretion of anti-cancer drugs from cells which have acquired resistance to such drugs, thereby to potentiate the effect of anti-cancer drugs and enhance the therapeutic effect of the anti-cancer drugs.

Where the 1,4-dihydropyridine derivative is used as an agent for overcoming resistance to anti-cancer drugs, the derivative is administered orally or parenterally (intramuscularly, subcutaneously, intravenously or as a suppository, etc.) simultaneously with or independently of anti-cancer drugs. The dose may vary depending upon the condition but is generally in the range of 1 to 9000 mg/day for adult, generally by dividing the daily dose into several doses of from 1 to 3000 mg.

Examples of anti-cancer drugs which may be used in combination with the derivatives of the present invention include chemotherapeutic agents used in ordinary cancer treatment such as vincristine, vinblastine, daunomycin, adriamycin, actinomycin D, aclacinomycin A, etoposide, bleomycin, peplomycin, cisplatin, methotrexate, 5-flurorouracil and their derivatives.

Furthermore, the 1,4-dihydropyridine derivatves may also be used in combination with the anti-cancer drugs described above before resistance to the drugs appears, thereby the enhance the therapeutic effect of the anti-cancer drugs.

In order to prepare pharmaceutical preparations of the compounds used in the present invention, the compounds are prepared into pharmacuetical preparations such as tablets, granules, powders, capsules, injections, suppositories, etc in a conventional manner.

For example in order to prepare oral preparations, excipients and if necessary, binders, disintegrators, lubricants, coloring agents, corrigents, etc. are added to the main ingredient (the agent for overcoming cancer resistance alone or a mixture thereof with anti-cancer drugs) and the resulting mixture is prepared into tablets, coated tablets, granules, capsules, etc.

Examples of excipient include lactose, corn starch, refined sugar, glucose sorbitol crystalline cellulose etc.; examples of binder include polyvinyl alcohol, polyvinyl ether, ethyl cellulose, methyl cellulose, gum arabic, tragacanth, gelatin, shellac, hydroxypropyl cellulose, hydroxypropyl starch, polyvinylpyrrolidone, etc.; examples of disintegrator include starch, agar, gelatin powder, crystalline cellulose, calcium carbonate, sodium hydrogencarbonate, calcium citrate, dextran, pectin, etc.; examples of lubricant include magnesium stearate, talc, polyethylene glycol, silica, hardened vegetable oil, etc.; examples of coloring agent are those which are permitted to be added to drugs; examples of the corrigent include cacao powder, menthol, borneol, cinnamon powders, etc. These tablets may be appropriately coated with sugar, gelatin and if necessary, with other coating agents.

Where injections are prepared, if necessary, pH adjusting agents, buffers, stabilizers, preservatives, etc. are added to the main ingredients (the agent for overcoming cancer-drug resistance alone or in admixture with an anti-cancer drug) and the resulting mixture is prepared into subcutaneous, intramuscular or intravenous injections in a conventional manner.

EXAMPLES

Embodiments of the invention are described below by way of example only.

EXAMPLE 1

Synthesis of 1,4-dihydro-4-(3,4-dimethoxyphenyl)-2,6-dimethyl-1-(3-phenylpropyl)-3,5-pyridinedicarboxylic acid 3-methyl-5-[3-(4-methylpiperazino)propyl]ester a) Synthesis of 1,4-dihydro-4-(3,4-dimethoxyphenyl)-2,6-dimethyl-3,5-pyridinecarboxylic acid 3-methyl-5-benzyl ester In 250 ml of benzene were dissolved 83.6 g (0.5 mol) of 3,4-dimethoxybenzaldehyde, 91.11 g (0.5 mol) of benzyl acetoacetate, 12.5 ml of piperidine and 12.5 ml of acetic acid. While removing azeotropic water, the mixture was heated to reflux for 3 hours. After 500 ml of ethyl acetate and 100 ml of water were added to the reaction mixture, the organic phase was washed successively with water, saturated aqueous sodium hydrogencarbonate solution and saturated aqueous sodium chloride. The organic phase was evaporated to dryness. To the resulting solid were added 57.57 g (0.5 mol) of methyl 3-aminocrotonate and 250 ml of ethanol. The mixture was heated to reflux for 12 hours. The solvent was distilled off and the residue was recrystallised from methanol to give 79.3 g of 1,4-dihydro-4-(3,4-dimethoxyphenyl)-2,6-dimethyl-3,5-pyridine-dicarboxylic acid 3-methyl-5-benzyl ester. Yield: 36%; Melting Point: 106°-107° C.

$^1$H NMR ($CDCl_3$): 7.20–7.28 (5H, m), 6.81 (1H, s), 6.71 (2H, t, J=8.4Hz), 4.98–5.18 (2H, m), 3.80 (3H, s), 3.67 (3H, s), 3.64 (3H, s) 2.35 (3H, s), 2.32 (3H, s).

MS m/z: 437 (M+).

b) Synthesis of 1,4-dihydro-4-(3,4-dimethoxyphenyl)-2,6-dimethyl-1-(3-phenylpropyl)-3,5-pyridinedicarboxylic acid 3-methyl-5-benzyl ester 10.92 g (25 mmols) of 1,4-dihydro-4-(3,4-dimethoxyphenyl)-2,6-dimethyl-3,5-pyridinedicarboxylic acid 3-methyl-5-benzyl ester was dissolved in 20 ml of anhydrous dimethylformamide. The solution was added dropwise to 1.31 g (30 mmols) of 60% sodium hydride suspended in 10 ml of anhydrous dimethylformamide under an argon atmosphere. After stirring at room temperature for 10 minutes, 10 ml of an anhydrous dimethylformamide solution of 5.97 g (30 mmols) of 3-phenylpropylbromide was added dropwise to the mixture followed by heating at 100° C. for 3 hours. Under ice cooling, diluted hydrochloric acid was added to the reaction mixture for neutralization. After 100 ml of water was added to the mixture, extraction was performed with ethyl acetate. After the organic phase was washed with water, the solvent was distilled off under reduced pressure. The thus obtained crude product was purified by silica gel chromatography (developing solvent: ethyl acetate-n-hexane=1:3) to give 6.51 g of 1,4-dihydro-4-(3,4-dimethoxyphenyl)-2,6-dimethyl-1-(3-phenyl-propyl)- 3,5-pyridinedicarboxylic acid 3-methyl-5-benzyl ester as oil. Yield: 47%

$^1$H NMR ($CDCl_3$): 7.18–7.30 (8H, m), 7.01–7.04 (2H, m), 6.73 (1H,s), 6.63 (2H, s), 5.14 (1H, s), 5.10–5.26 (2H, m), 3.75 (3H, s), 3.70 (3H, s), 3.61 (3H, s),2.39–2.44 (2H, m), 1.70–1.77 (2H, m).

MS m/z: 555 (M+).

c) Synthesis of 1,4-dihydro-4-(3,4-dimethoxyphenyl)-2,6-dimethyl-1-(3-phenylpropyl)-3,5-pyridinedicarboxylic acid 3-methyl ester After 6.51 g (12.0 mmols) of 1,4-dihydro-4-(3,4-dimethoxy-phenyl)-2,6-dimethyl-1-(3-phenylpropyl)-3,5-pyridine-dicarboxylic acid 3-methyl-5-benzyl ester was dissolved in 60 ml of methanol, the solution was stirred for 2 hours in a hydrogen atmosphere in the presence of 650 mg of 5% palladium/carbon. The catalyst was removed by filtration. The solvent was then removed under reduced pressure to give 5.19 g of 1,4-dihydro-4-(3,4-dimethoxyphenyl)-2,6-dimethyl-1-(3-phenylpropyl)-3,5-pyridinedicarboxylic acid 3-methyl ester. Yield: 93%. The product was used for the next reaction without further purification.

$^1$H NMR ($CDCl_3$): 7.24–7.29 (3H, m), 7.02 (2H, d, J=6.9Hz), 6.83 (1H, s), 6.67 (2H, s), 5.13 (1H, s), 3.76 (6H, s), 3.71 (3H, s), 3.58–3.65 (2H, m), 2.40 (3H, s), 2.42 (3H, s), 2.31–2.50 (2H, m), 1.65–1.79 (2H, m).

MS m/z: 465 (M+).

d) Synthesis of 1,4-dihydro-4-(3,4-dimethoxyphenyl)-2,6-dimethyl-1-(3-phenylpropyl)-3,5-pyridinedicarboxylic acid 3-methyl-5-[3-(4-methylpiperazino)propyl] ester After 0.98 g (3.85 mmols ) of 1-methyl-2-chloropyridinium iodide was slowly added to a dichloromethane solution of 1.63 g (3.5 mmols) of 1,4-dihydro-4-(3,4-dimethoxyphenyl)-2,6-dimethyl-1-(3-phenylpropyl)-3,5-pyridinedicarboxylic acid 3-methyl ester, 0.61 g (3.85 mmols) of 1-(3-hydroxypropyl)-4-methylpiperazine and 1.16 ml (8.40 mmols) of triethylamine, the mixture was heated to reflux for an hour. After the solvent was distilled off under reduced pressure, ethyl acetate was added to the residue. After washing with water, the solvent was distilled off under reduced pressure. The obtained residue was purified by alumina column chromatography (developing solvent ethyl acetate-*n*-hexane=1:2) to give 1.42 g of 1,4-dihydro-4-(3,4-dimethoxyphenyl)-2,6-dimethyl-1-(3-phenylpropyl)-3,5-pyridinedicarboxylic acid 3-methyl-5-[3-(4-methylpiperazino)propyl] ester as oil. Yield: 65%

$^1H$ NMR ($CDCl_3$): 7.18–7.28 (3H, m), 7.03 (2H, d, J=6.9Hz), 5.09 (1H, s) 4.13–4.18 (2H, m), 3.76 (3H, s), 3.74 (3H, s), 3.71 (3H, s), 3.58–3.63 (2H, t, J=7.8Hz), 2.33–2.46 (8H, m), 2.35–2.46 (8H, m), 2.35 (3H, s), 2.33 (3H, s), 1.67–1.84 (2H, m ).

MS m/z: 605 (M+).

EXAMPLES 2 to 32

Compounds shown at Column a) in Tables 1 to 4 were synthesized in a manner similar to Example 1 except that the amino alcohols shown at Column b) in Tables 1 to 4 were used in place of 1-(3-hydroxypropyl)-4-methylpiperazine.

TABLE 1

Structure

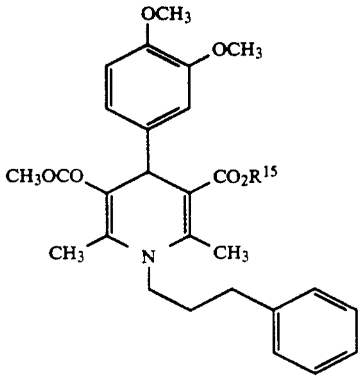

| No. | a) compound | b) amino-alcohol | $R_{15}$ = | $IC_{50}$ ng/ml |
|---|---|---|---|---|
| 1 | 1,4-dihydro-4-(3,4-dimethoxyphenyl)-2,6-dimethyl-1-(3-phenylpropyl)-3,5-pyridinedicarboxylic acid 3-methyl-5-[3-(4-methylpiperazino)propyl]ester | 1-(3-hydroxypropyl)-4-methylpiperazine | 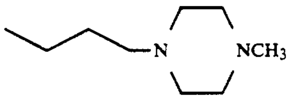 | 0.15 |
| 2 | 1,4-dihydro-4-(3,4-dimethoxyphenyl)-2,6-dimethyl-1-(3-phenylpropyl)-3,5-pyridinedicarboxylic acid 3-methyl-5-[3-(4-isopropylpiperazino)propyl]ester | 1-(3-hydroxypropyl)-4-isopropylpiperazine | 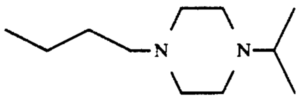 | 0.80 |
| 3 | 1,4-dihydro-4-(3,4-dimethoxyphenyl)-2,6-dimethyl-1-(3-phenylpropyl)-3,5-pyridinedicarboxylic acid 3-methyl-5-[3-(4-isobutylpiperazino)propyl]ester | 1-(3-hydroxypropyl)-4-isobutylpiperazine | 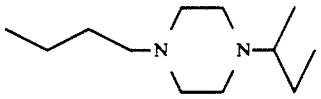 | 1.50 |
| 4 | 1,4-dihydro-4-(3,4-dimethoxyphenyl)-2,6-dimethyl-1-(3-phenylpropyl)-3,5-pyridinedicarboxylic acid 3-methyl-5-[3-(4-benzylpiperazino)propyl]ester | 1-(3-hydroxypropyl)-4-benzylpiperazine | 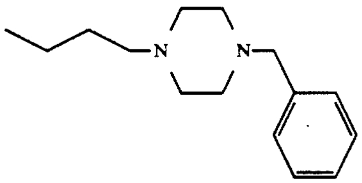 | 0.50 |
| 5 | 1,4-dihydro-4-(3,4-dimethoxyphenyl)-2,6-dimethyl-1-(3-phenylpropyl)-3,5-pyridinedicarboxylic acid 3-methyl-5-[3-(4-diphenylmethylpiperazino)propyl]ester | 1-(3-hydroxypropyl)-4-diphenylmethylpiperazine | 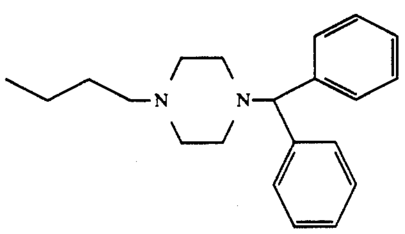 | 1.00 |

TABLE 1-continued

Structure

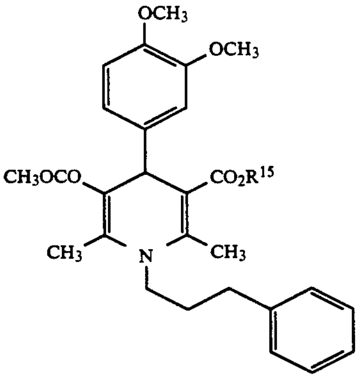

| No. | a) compound | b) amino-alcohol | $R_{15}$ = | $IC_{50}$ ng/ml |
|---|---|---|---|---|
| 6 | 1,4-dihydro-4-(3,4-dimethoxyphenyl)-2,6-dimethyl-1-(3-phenylpropyl)-3,5-pyridinedicarboxylic acid 3-methyl-5-[3-(4-(dibenzosuberan-5-yl)-piperazino)propyl]ester | 1-(3-hydroxy-propyl)-4-(di-benzosuberan-5-yl)piperazine | 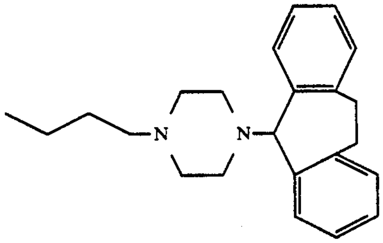 | 0.60 |
| 7 | 1,4-dihydro-4-(3,4-dimethoxyphenyl)-2,6-dimethyl-1-(3-phenylpropyl)-3,5-pyridinedicarboxylic acid 3-methyl-5-[3-(4-phenylpiperazino)propyl]ester | 1-(3-hy-droxypropyl)-4-phenyl-piperazine | 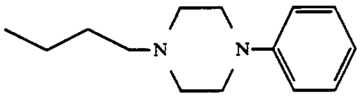 | 1.90 |
| 8 | 1,4-dihydro-4-(3,4-dimethoxyphenyl)-2,6-dimethyl-1-(3-phenylpropyl)-3,5-pyridinedicarboxylic acid 3-methyl-5-[3-(4-(pyridin-2-yl)piperazino]propyl]ester | 1-(3-hy-droxypropyl)-4-(pyridin-2-yl)piperazine | 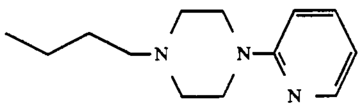 | 0.38 |

TABLE 2

Structure

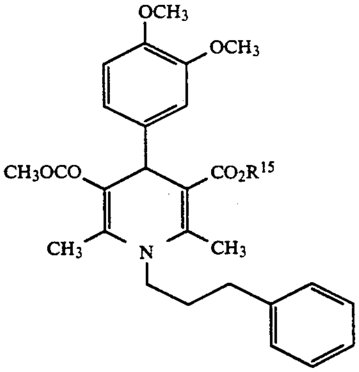

| No. | a) compound | b) amino-alcohol | $R_{15}$ = | $IC_{50}$ ng/ml |
|---|---|---|---|---|
| 9 | 1,4-dihydro-4-(3,4-dimethoxyphenyl)-2,6-dimethyl-1-(3-phenylpropyl)-3,5-pyridinedicarboxylic acid 3-methyl-5-[3-(4-(2-pyrimidyl)piperazino)propyl]ester | 1-(3-hy-droxypropyl)-4-(2-pyrim-idyl)piperazine | 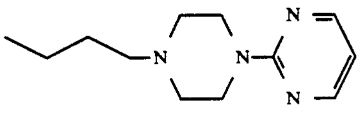 | 1.00 |
| 10 | 1,4-dihydro-4-(3,4-dimethoxyphenyl)-2,6-dimethyl-1-(3-phenylpropyl)-3,5-pyridinedicarboxylic acid 3-methyl-5-[3-(4-carboethoxypiperazino)propyl]ester | 1-(3-hy-droxypropyl)-4-carboethoxy piperazine | 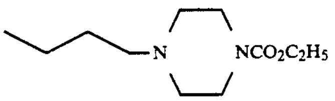 | 0.25 |

TABLE 2-continued

Structure

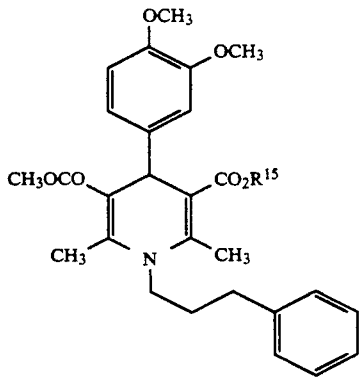

| No. | a) compound | b) amino-alcohol | $R_{15}$ = | $IC_{50}$ ng/ml |
|---|---|---|---|---|
| 11 | 1,4-dihydro-4-(3,4-dimethoxyphenyl)-2,6-dimethyl-1-(3-phenylpropyl)-3,5-pyridinedicarboxylic acid 3-methyl-5-[2-(4-methylpiperazino)ethyl]ester | 1-(2-hydroxyethyl)-4-methyl piperazine | 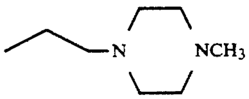 | 0.80 |
| 12 | 1,4-dihydro-4-(3,4-dimethoxyphenyl)-2,6-dimethyl-1-(3-phenylpropyl)-3,5-pyridinedicarboxylic acid 3-methyl-5-[4-(4-methylpiperazino)butyl]ester | 1-(4-hydroxybutyl)-4-methyl piperazine | 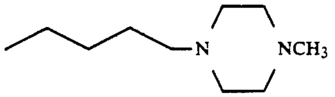 | 0.14 |
| 13 | 1,4-dihydro-4-(3,4-dimethoxyphenyl)-2,6-dimethyl-1-(3-phenylpropyl)-3,5-pyridinedicarboxylic acid 3-methyl-5-(3-morpholinopropyl)]ester | 1-(3-hydroxypropyl)-morpholine | 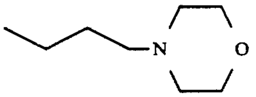 | 0.55 |
| 14 | 1,4-dihydro-4-(3,4-dimethoxyphenyl)-2,6-dimethyl-1-(3-phenylpropyl)-3,5-pyridinedicarboxylic acid 3-methyl-5-(2-morpholinoethyl)]ester | 1-(2-hydroxy ethyl)morpholine | 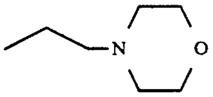 | 0.60 |
| 15 | 1,4-dihydro-4-(3,4-dimethoxyphenyl)-2,6-dimethyl-1-(3-phenylpropyl)-3,5-pyridinedicarboxylic acid 3-methyl-5-[2-(4-piperidino)piperidinoethyl]ester | 1-(2-hydroxy ethyl)-4-piperidino-piperidine | 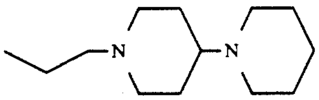 | 0.80 |
| 16 | 1,4-dihydro-4-(3,4-dimethoxyphenyl)-2,6-dimethyl-1-(3-phenylpropyl)-3,5-pyridinedicarboxylic acid 3-methyl-5-[3-(dimethylamino)propyl]ester | 3-(dimethylamino)-propanol | 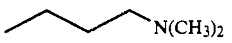 | 0.65 |

TABLE 3

Structure

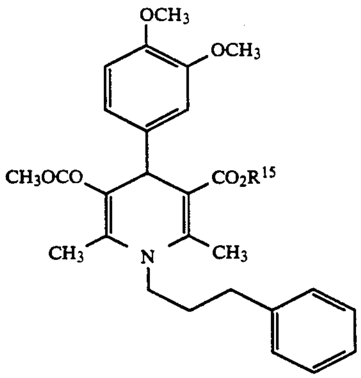

| No. | a) compound | b) amino-alcohol | $R_{15}$ = | $IC_{50}$ ng/ml |
|---|---|---|---|---|
| 17 | 1,4-dihydro-4-(3,4-dimethoxyphenyl)-2,6-dimethyl-1-(3-phenylpropyl)-3,5-pyridinedicarboxylic acid 3-methyl-5-[3-(benzylmethylamino)propyl]ester | 3-(benzylmethylamino)-1-propanol | 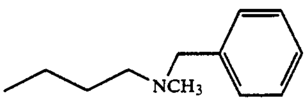 | 0.38 |
| 18 | 1,4-dihydro-4-(3,4-dimethoxyphenyl)-2,6-dimethyl-1-(3-phenylpropyl)-3,5-pyridinedicarboxylic acid 3-methyl-5-[3-(2-pyridyl)propyl]ester | 3-(2-pyridyl)-1-propanol | 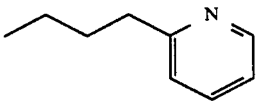 | 2.50 |
| 19 | 1,4-dihydro-4-(3,4-dimethoxyphenyl)-2,6-dimethyl-1-(3-phenylpropyl)-3,5-pyridinedicarboxylic acid 3-methyl-5-[3-(3-pyridyl)propyl]ester | 3-(3-pyridyl)-1-propanol | 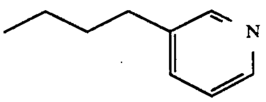 | 0.19 |
| 20 | 1,4-dihydro-4-(3,4-dimethoxyphenyl)-2,6-dimethyl-1-(3-phenylpropyl)-3,5-pyridinedicarboxylic acid 3-methyl-5-[3-(4-pyridyl)propyl]ester | 3-(4-pyridyl)-1-propanol | 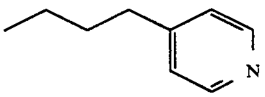 | 1.90 |
| 21 | 1,4-dihydro-4-(3,4-dimethoxyphenyl)-2,6-dimethyl-1-(3-phenylpropyl)-3,5-pyridinedicarboxylic acid 3-methyl-5-[3-(6-methylpyridin-2-yl)propyl]ester | 3-(6-methylpyridin-2-yl)-1-propanol | 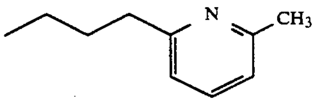 | 0.32 |
| 22 | 1,4-dihydro-4-(3,4-dimethoxyphenyl)-2,6-dimethyl-1-(3-phenylpropyl)-3,5-pyridinedicarboxylic acid 3-methyl-5-[2-(2-pyridyl)ethyl]ester | 2-(2-pyridyl)ethanol | 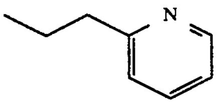 | 0.32 |
| 23 | 1,4-dihydro-4-(3,4-dimethoxyphenyl)-2,6-dimethyl-1-(3-phenylpropyl)-3,5-pyridinedicarboxylic acid 3-methyl-5-(4-pyridylmethyl)ester | 4-pyridinemethanol | 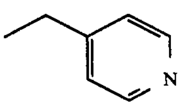 | 0.60 |
| 24 | 1,4-dihydro-4-(3,4-dimethoxyphenyl)-2,6-dimethyl-1-(3-phenylpropyl)-3,5-pyridinedicarboxylic acid 3-methyl-5-[2-(3-(6-methyl-2-pyridyl)propyloxy)-ethyl]ester | 2-[3-(6-methyl-2-pyridyl)propyloxy]ethanol | 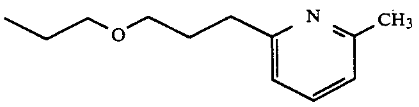 | 0.90 |

TABLE 4

Structure

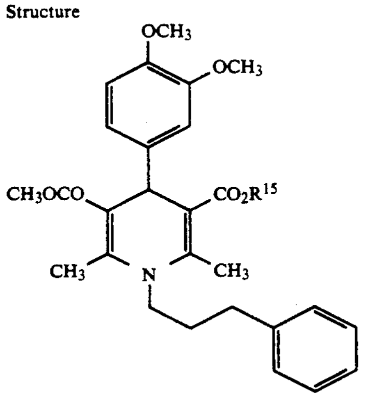

| No. | a) compound | b) amino-alcohol | $R_{15}$ = | $IC_{50}$ ng/ml |
|---|---|---|---|---|
| 25 | 1,4-dihydro-4-(3,4-dimethoxyphenyl)-2,6-dimethyl-1-(3-phenylpropyl)-3,5-pyridinedicarboxylic acid 3-methyl-5-(4-morpholinobutyl)]ester | 1-(4-hydroxybutyl)-morpholine | 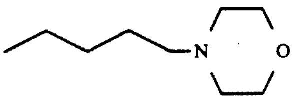 | 0.50 |
| 26 | 1,4-dihydro-4-(3,4-dimethoxyphenyl)-2,6-dimethyl-1-(3-phenylpropyl)-3,5-pyridinedicarboxylic acid 3-methyl-5-[3-(4-(2-chlorophenyl)piperazino)propyl]ester | 1-(3-hydroxypropyl-4-(2-chlorophenyl)piperazine | 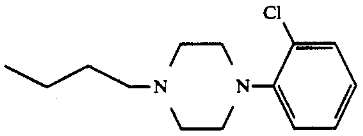 | 0.31 |
| 27 | 1,4-dihydro-4-(3,4-dimethoxyphenyl)-2,6-dimethyl-1-(3-phenylpropyl)-3,5-pyridinedicarboxylic acid 3-methyl-5-[3-(4-(4-fluorophenyl)piperazino)-propyl]ester | 1-(3-hydroxy-propyl)-4-(4-fluorophenyl) piperazine | 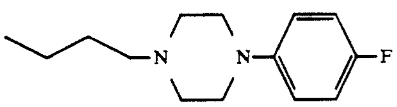 | 0.29 |
| 28 | 1,4-dihydro-4-(3,4-dimethoxyphenyl)-2,6-dimethyl-1-(3-phenylpropyl)-3,5-pyridinedicarboxylic acid 3-methyl-5-[3-(4-phenyl-piperazino)propyl]ester | 1-(2,3-dihydroxypropyl)-4-phenyl piperzine | 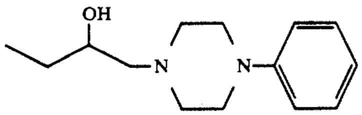 | 0.21 |
| 29 | 1,4-dihydro-4-(3,4-dimethoxyphenyl)-2,6-dimethyl-1-(3-phenylpropyl)-3,5-pyridinedicarboxylic acid 3-methyl-5-(3-piperazinopropyl)ester | 1-(3-hydroxypropyl) piperazine | 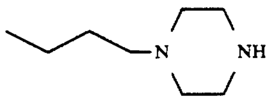 | 14.0 |
| 30 | 1,4-dihydro-4-(3,4-dimethoxyphenyl)-2,6-dimethyl-1-(3-phenylpropyl)-3,5-pyridinedicarboxylic acid 3-methyl-5-(2-hydroxy-3-morpholinopropyl)]ester | 1-(2,3-dihydroxypropyl)-morpholine | 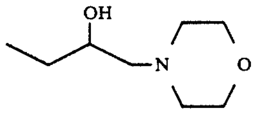 | 2.10 |
| 31 | 1,4-dihydro-4-(3,4-dimethoxyphenyl)-2,6-dimethyl-1-(3-phenylpropyl)-3,5-pyridinedicarboxylic acid 3-methyl-5-[3-(4-(2-trifluoromethylphenyl)piperazino)-propyl]ester | 1-(3-hydroxy-propyl)-4-(2-trifluoromethyl-phenyl)piperazine | 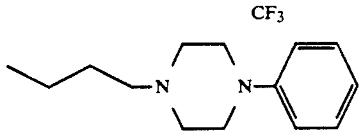 | 1.00 |
| 32 | 1,4-dihydro-4-(3,4-dimethoxyphenyl)-2,6-dimethyl-1-(3-phenylpropyl)-3,5-pyridinedicarboxylic acid 3-methyl-5-[3-(4-acetyl-piperazino)propyl]ester | 1-(3-hydroxy-propyl)-4-acetylpiperazine | 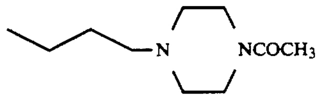 | 0.50 |

EXAMPLE 33

Synthesis of 1,4-dihydro-4-(3,4-dimethoxyphenyl)-2,6-dimethyl-1-(3-phenylpropyl)-3,5-pyridinedicarboxylic acid 3-methyl ester-5-(2-pyridin-2-yl)ethylamide In 3 ml of dichloromethane was dissolved 176 mg (1.1 mmol) of 1,1-carbonyl diimidazole and 465 mg (1.0 mmol) of 1 4-dihydro-4-(3,4-dimethoxyphenyl)-2,6-dimethyl-1-(3-phenylpropyl)-3,5-pyridinedicarboxylic acid 3-methyl ester synthesized by the method shown in Example 1. The mixture was heated to reflux for 10 minutes. After cooling to room temperature, 1 ml of dichloromethane solution of 128 mg (1.05 mmol) of 2-(2-pyridyl)ethylamine was added dropwise and the mixture was stirred at room temperature for further 10 minutes. To the reaction solution was added 10 ml of water and the product was extracted with ethyl acetate. The solvent was distilled off under reduced pressure. The residue was purified by silica gel chromatography (developing solvent: ethyl acetate-n-hexane=1:1) to give 467 mg of 1,4-dihydro-4-(3,4-dimethoxyphenyl)-2,6-dimethyl-1-(3-phenylpropyl)-3,5-pyridinedicarboxylic acid 3-methyl ester-5-(2-pyridin-2-yl)ethylamide as oil. Yield: 82%

$^1H$ NMR ($CDCl_3$): 8.33 (1H, d, J=4.8Hz), 7.52 (1H, t, J=6.0Hz), 7.0-7.26 (7H, m), 6.73 (1H, s), 6.61 (2H, s), 6.19 (1H, s), 4.66 (1H, s), 3.76 (3H, s), 3.66 (6H, s), 3.52-3.65 (4H, m), 2.90 (2H, t, J=7.2Hz), 2.49 g (2H, t, J=7.2Hz), 1.65-180 (2H, m).

MS m/z: 569 ($M^+$).

EXAMPLE 34

The second compound shown at Column a) in Table 5 was synthesised in a manner similar to Example 33 except for using the amine shown at Column b) in Table 5 in place of 2-(2-pyridyl)ethylamine.

TABLE 5

Structure

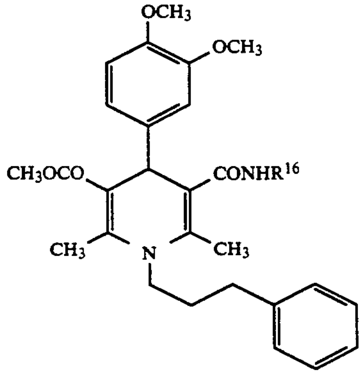

| No. | a) compound | b) amino | $R_{16}$ = | $IC_{50}$ ng/ml |
|---|---|---|---|---|
| 33 | 1,4-dihydro-4-(3,4-dimethoxyphenyl)-2,6-dimethyl-1-(3-phenylpropyl)-3,5-pyridinedicarboxylic acid 3-methylester-5-[2-(2-pyridyl)ethyl]amide | 2-(2-pyridyl)-ethylamine | 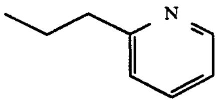 | 15.0 |
| 34 | 1,4-dihydro-4-(3,4-dimethoxyphenyl)-2,6-dimethyl-1-(3-phenylpropyl)-3,5-pyridinedicarboxylic acid 3-methylester-5-(2-pyridyl)ethyl]amide | 2-pyridylmethylamine | 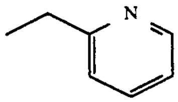 | 4.00 |

EXAMPLES 35 to 52

Compounds shown at Column a) in Tables 6 to 8 were synthesized in a manner similar to Example 1 except that the amino alcohols shown at Column b) in Tables 6 to 8 were used in place of 1-(3-hydroxypropyl)4-methyl piperazine and the halides shown in Column c) were used in place of 3-phenylpropylbromide.

TABLE 6

Structure

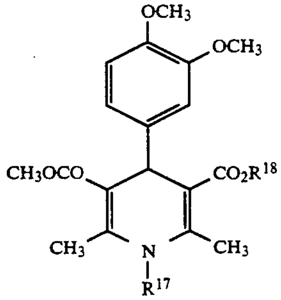

| No. | a) compound | b) halide | c) amino alcohol | | $IC_{50}$ ng/ml |
|---|---|---|---|---|---|
| 35 | 1,4-dihydro-4-(3,4-dimethoxyphenyl)-2,6-dimethyl-1-(3-phenoxypropyl)-3,5-pyridinedicarboxylic acid 3-methyl-5-[3-(4-methylpiperazino)propyl]ester | 3-phenoxypropylbromide | 1-(3-hydroxypropyl)-4-methylpiperazine | $R_{17}$ = 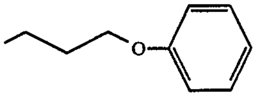 $R_{18}$ = 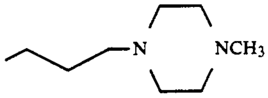 | 0.65 |

TABLE 6-continued

| No. | a) compound | b) halide | c) amino alcohol | Structure 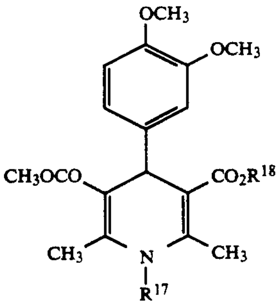 | $IC_{50}$ ng/ml |
|---|---|---|---|---|---|
| 36 | 1,4-dihydro-4-(3,4-dimethoxyphenyl)-2,6-dimethyl-1-(3-phenoxypropyl)-3,5-pyridinedicarboxylic acid 3-methyl-5-[3-(3-pyridyl)propyl]ester | 3-phenoxypropylbromide | 3-(3-pyridyl)-1-propanol | $R_{17}$ = 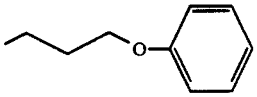 $R_{18}$ = 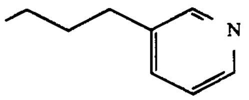 | 0.60 |
| 37 | 1,4-dihydro-4-(3,4-dimethoxyphenyl)-2,6-dimethyl-1-(2-phenoxyethyl)-3,5-pyridinedicarboxylic acid 3-methyl-5-[3-(4-methylpiperazino)propyl]ester | 2-phenoxyethylchloride | 1-(3-hydroxypropyl)-4-methylpiperazine | $R_{17}$ = 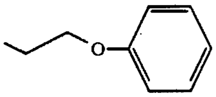 $R_{18}$ = 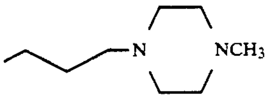 | 0.85 |
| 38 | 1,4-dihydro-4-(3,4-dimethoxyphenyl)-2,6-dimethyl-1-(2-phenoxypropyl)-3,5-pyridinedicarboxylic acid 3-methyl-5-[3-(3-pyridyl)propyl]ester | 2-phenoxyethylchloride | 3-(3-pyridyl)-1-propanol | $R_{17}$ = 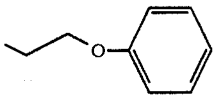 $R_{18}$ = 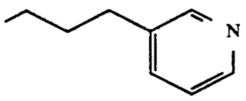 | 0.70 |
| 39 | 1,4-dihydro-4-(3,4-dimethoxyphenyl)-2,6-dimethyl-1-[3-(1-naphthoxy)propyl]-3,5-pyridinedicarboxylic acid 3-methyl-5-[3-(4-methylpiperazino)propyl]ester | 3-(1-naphthoxy)propylbromide | 1-(3-hydroxypropyl)-4-methylpiperazine | $R_{17}$ = 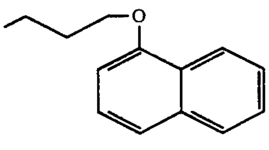 $R_{18}$ = 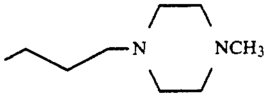 | 1.50 |

TABLE 6-continued

| No. | a) compound | b) halide | c) amino alcohol | Structure<br>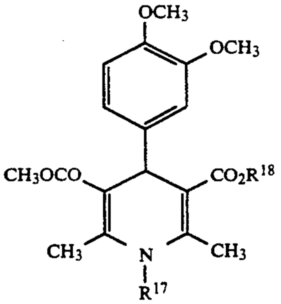 | $IC_{50}$ ng/ml |
|---|---|---|---|---|---|
| 40 | 1,4-dihydro-4-(3,4-dimethoxyphenyl)-2,6-dimethyl-1-[3-(1-naphthoxy)propyl]-3,5-pyridinedicarboxylic acid 3-methyl-5-[3-(3-pyridyl)propyl]ester | 3-(1-naphthoxy)-propyl-bromide | 3-(3-pyridyl)-1-propanol | $R_{17}$ = 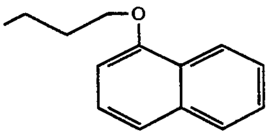<br>$R_{18}$ = 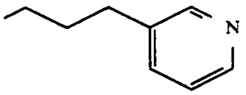 | 3.50 |

TABLE 7

| No. | a) compound | b) halide | c) amino alcohol | Structure<br>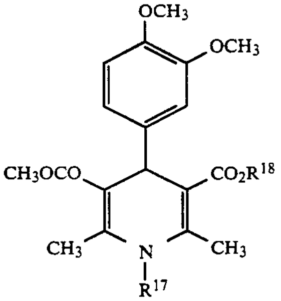 | $IC_{50}$ ng/ml |
|---|---|---|---|---|---|
| 41 | 1,4-dihydro-4-(3,4-dimethoxyphenyl)-2,6-dimethyl-1-[3-(2-naphthoxy)propyl]-3,5-pyridinedicarboxylic acid 3-methyl-5-[3-(4-methylpiperazino)propyl]ester | 3-(2-naphthoxy)-propyl-bromide | 1-(3-hydroxypropyl)-4-methyl-piperazine | $R_{17}$ = 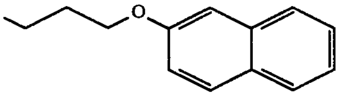<br>$R_{18}$ = 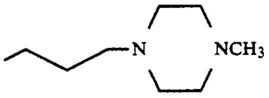 | 1.30 |
| 42 | 1,4-dihydro-4-(3,4-dimethoxyphenyl)-2,6-dimethyl-1-[3-(2-naphthoxy)propyl]-3,5-pyridinedicarboxylic acid 3-methyl-5-[3-(3-pyridyl)propyl]ester | 3-(2-naphthoxy)-propyl-bromide | 3-(3-pyridyl)-1-propanol | $R_{17}$ = 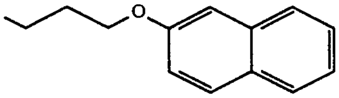<br>$R_{18}$ = 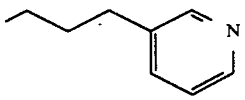 | 4.00 |

TABLE 7-continued

| No. | a) compound | b) halide | c) amino alcohol | Structure<br>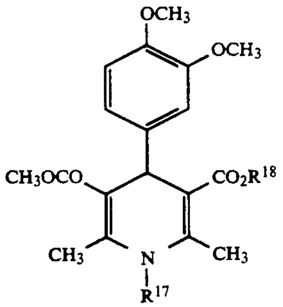 | $IC_{50}$ ng/ml |
|---|---|---|---|---|---|
| 43 | 1,4-dihydro-4-(3,4-dimethoxyphenyl)-2,6-dimethyl-1-(3,3-diphenylpropyl)-3,5-pyridinedicarboxylic acid 3-methyl-5-[3-(4-methylpiperazino)-propyl]ester | 3,3-diphenylpropyl-bromide | 1-(3-hydroxypropyl)-4-methyl-piperazine | $R_{17}$ = 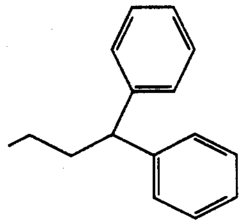<br>$R_{18}$ = 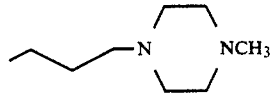 | 0.18 |
| 44 | 1,4-dihydro-4-(3,4-dimethoxyphenyl)-2,6-dimethyl-1-[3-(2-naphthoxy)propyl]-3,5-pyridine-dicarboxylic acid 3-methyl-5-[3-(3-pyridyl)propyl]ester | 3,3-diphenyl-propyl-bromide | 3-(3-pyridyl)-1-propanol | $R_{17}$ = 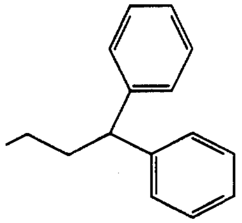<br>$R_{18}$ = 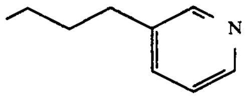 | 0.80 |
| 45 | 1,4-dihydro-4-(3,4-dimethoxyphenyl)-2,6-dimethyl-1-[3-(4-phenoxyphenoxy)propyl]-3,5-pyridinedicarboxylic acid 3-methyl-5-[3-(4-methylpiperazino)propyl]ester | 3-(4-phenoxy-phenoxy)-propyl-bromide | 1-(3-hydroxypropyl)-4-methyl-piperazine | $R_{17}$ = 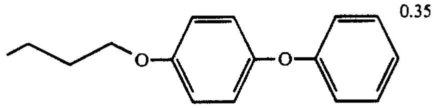<br>$R_{18}$ = 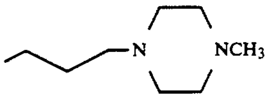 | 0.35 |
| 46 | 1,4-dihydro-4-(3,4-dimethoxyphenyl)-2,6-dimethyl-1-[3-(2-naphthoxy)propyl]-3,5-pyridine-dicarboxylic acid 3-methyl-5-[3-(3-pyridyl)propyl]ester | 3-(4-phenoxy-phenoxy)-propyl-bromide | 3-(3-pyridyl)-1-propanol | $R_{17}$ = 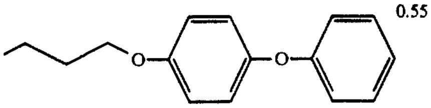<br>$R_{18}$ = 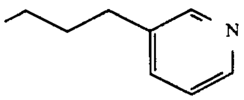 | 0.55 |

TABLE 8

| No. | a) compound | b) halide | c) amino alcohol | Structure<br>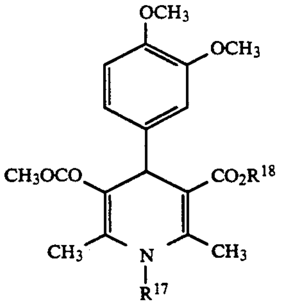 | $IC_{50}$ ng/ml |
|---|---|---|---|---|---|
| 47 | 1,4-dihydro-4-(3,4-dimethoxyphenyl)-2,6-dimethyl-1-[3-(4-fluorophenoxy)propyl]-3,5-pyridinedicarboxylic acid 3-methyl-5-[3-(4-phenylpiperazino)propyl]ester | 3-(4-fluoro-phenoxy)-propyl-bromide | 1-(3-hy-droxypro-pyl)-4-phenyl-piperazine | $R_{17}$ = 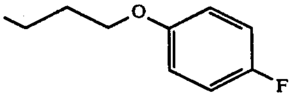<br>$R_{18}$ = 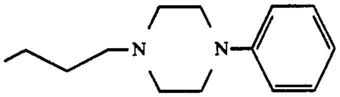 | 0.20 |
| 48 | 1,4-dihydro-4-(3,4-dimethoxyphenyl)-2,6-dimethyl-1-[3-(4-phenylphenoxy)propyl]-3,5-pyridinedicarboxylic acid 3-methyl-5-[3-(4-methylpiperazino)propyl]ester | 3-(4-phenyl-phenoxy)-propyl-bromide | 1-(3-hy-droxypro-pyl)-4-methyl-piperazine | $R_{17}$ = 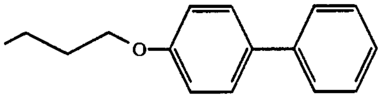<br>$R_{18}$ = 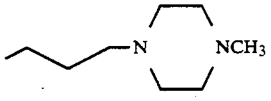 | 0.70 |
| 49 | 1,4-dihydro-4-(3,4-dimethoxyphenyl)-2,6-dimethyl-1-(3,3-diphenylpropyl]-3,5-pyridinedicarboxylic acid 3-methyl-5-[3-(4-(2-pyridyl)piperazino)propyl]ester | 3,3-diphenyl-propyl-bromide | 1-(3-hy-droxypro-pyl)-4-(2-pyridyl) piperazine | $R_{17}$ = 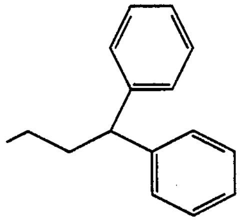<br>$R_{18}$ = 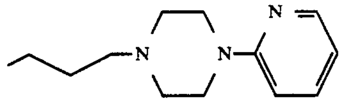 | 0.48 |
| 50 | 1,4-dihydro-4-(3,4-dimethoxyphenyl)-2,6-dimethyl-1-(3,3-diphenylpropyl]-3,5-pyridinedicarboxylic acid 3-methyl-5-[3-(4-phenylpiperazino)propyl]ester | 3,3-diphenyl-propyl-bromide | 1-(3-hy-droxypro-pyl)-4-phenyl-piperazine | $R_{17}$ = 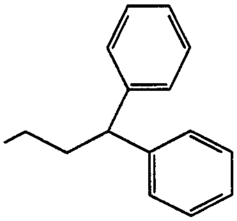<br>$R_{18}$ = 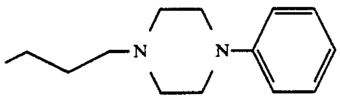 | 0.65 |

TABLE 8-continued

| No. | a) compound | b) halide | c) amino alcohol | Structure 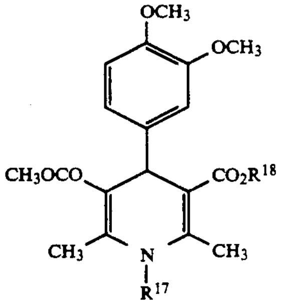 | $IC_{50}$ ng/ml |
|---|---|---|---|---|---|
| 51 | 1,4-dihydro-4-(3,4-dimethoxyphenyl)-2,6-dimethyl-1-[3-(2-fluorophenoxy)propyl]-3,5-pyridinedicarboxylic acid 3-methyl-5-[3-(3-pyridyl)propyl]ester | 3-(2-fluorophenoxy)-propylbromide | 3-(3-pyridyl)-1-propanol | $R_{17}$ = 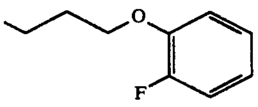 $R_{18}$ = 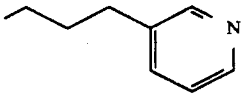 | 0.80 |
| 52 | 1,4-dihydro-4-(3,4-dimethoxyphenyl)-2,6-dimethyl-1-[3-(2-fluorophenoxy)propyl]-3,5-pyridinedicarboxylic acid 3-methyl-5-[3-(4-methylpiperazino)propyl]ester | 3-(2-fluorophenoxy) propylbromide | 1-(3-hydroxypropyl)-4-methylpiperazine | $R_{17}$ = 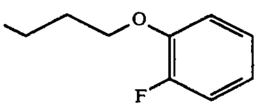 $R_{18}$ = 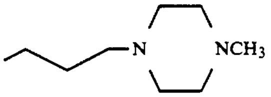 | 0.70 |

EXAMPLE 53

Synthesis of 1,4-dihydro-4-(3,4-dimethoxyphenyl)-2,6-dimethyl-1-(3-benzyloxypropyl)-3,5-pyridinedicarboxylic acid 3-methyl-5-[3-(4-methylpiperazino)propyl]ester After 2.15 g (4.2 mmols) of 1,4-dihydro-4-(3,4-dimethoxy-phenyl)-2,6-dimethyl-1-(3-benzyloxypropyl)-3,5-pyridine-dicarboxylic acid 3,5-dimethyl ester prepared by the process described in Japanese Patent Application Laid Open No. 1-316357 was dissolved in 8 ml of dimethylsulfoxide, 320 mg (4.9 mmols) of potassium hydroxide dissolved in 0.5 ml of water was added to the solution. The mixture was heated at 100° C. for 5 hours. After the solvent was distilled off under reduced pressure, 10 ml of water was added to the residue followed by extraction twice with ethyl acetate. After the aqueous phase was rendered acidic with diluted hydrochloric acid, extraction was performed 3 times with chloroform. After washing with water, the extract was concentrated and the obtained residue was purified by silica gel column chromatography (developing solvent: ethyl acetate-n-hexane=1:1) to give 875 mg of 1,4-dihydro-4-(3,4-dimethoxyphenyl)-2,6-dimethyl-1-(3-benzyloxypropyl)-3,5-pyridinedicarboxylic acid 3-methyl ester as an oil. Yield, 42%. The obtained monocarboxylic acid was esterified by the method described in Example 1 to give 1,4-dihydro-4-(3,4-dimethoxyphenyl)-2,6-dimethyl-1-(3-benzyloxypropyl)-3,5-pyridine-dicarboxylic acid 3-methyl-5-[3 -(4-methylpiperazino)propyl] ester. Yield: 72%.

$^1$H NMR ($CDCl_3$): 7.21–7.38 (5H, m) 6.81 (1H, s) 6.67 (2H, m) 5.14 (1H, s) 4.32 (2H, s) 4.15–4.22 (2H, m) 3.79 (3H, s) 3.77 (3H, s) 3.71 (3H, s) 3.03–3.09 (2H, m) 2.49 (6H, s) 2.36–2.48 (4H, m) 2.28 (3H, s) 1.78–1.83 (2H, m) 1.53–1.63 (2H, m).

MS m/z 635 (M+).

EXAMPLE 54

The second compound shown at Column a) in Table 9 was synthesised in a manner similar to Example 53 except for using the aminoalcohol shown at Column b) in Table 9 in place of 1-(3-hydroxypropyl)-4-methylpiperazine.

TABLE 9

Structure

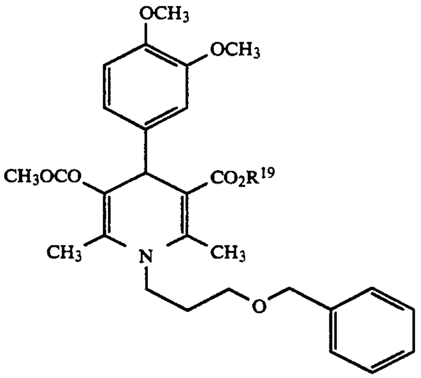

| No. | a) compound | b) amino-alcohol | $R_{19}$ = | |
|---|---|---|---|---|
| 53 | 1,4-dihydro-4-(3,4-dimethoxyphenyl)-2,6-dimethyl-1-(3-benzyloxypropyl)-3,5-pyridinedicarboxylic acid 3-methyl-5-[3-(4-methylpiperazino)propyl]ester | 1-(3-hydroxypropyl)-4-methylpiperazine | 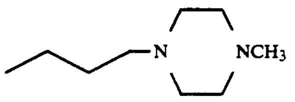 | 0.50 |
| 54 | 1,4-dihydro-4-(3,4-dimethoxyphenyl)-2,6-dimethyl-1-(3-benzyloxypropyl)-3,5-pyridinedicarboxylic acid 3-methyl-5-[3-(3-pyridyl)propyl]ester | 3-(3-pyridyl)-1-propanol | 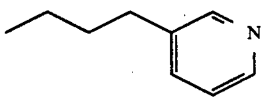 | 0.33 |

EXAMPLES 55 to 58

Compounds shown at Column a) in Table 10 were synthesised in a manner similar to Example 1 except for using the aldehydes shown at Column b) in Table 10 in place of 3,4-dimethoxybenzaldehyde and the amino alcohol shown at Column c) in Table 10 in place of 1-(3-hydroxypropyl)-4-methylpiperazine.

TABLE 10

Structure

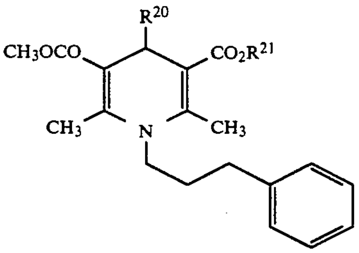

| No. | a) compound | b) aldehyde | c) amino alcohol | | $IC_{50}$ ng/ml |
|---|---|---|---|---|---|
| 55 | 1,4-dihydro-4-phenyl-2,6-dimethyl-1-(3-phenylpropyl)-3,5-pyridinedicarboxylic acid 3-methyl-5-[3-(4-methylpiperazino)propyl]ester | benzaldehyde | 1-(3-hydroxypropyl)-4-methylpiperazine | $R_{20}$ = 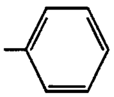<br>$R_{21}$ = 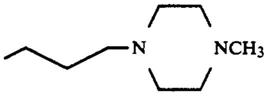 | 0.40 |
| 56 | 1,4-dihydro-4-phenyl-2,6-dimethyl-1-(3-phenylpropyl)-3,5-pyridinedicarboxylic acid 3-methyl-5-[3-(3-pyridyl)-propyl]ester | benzaldehyde | 3-(3-pyridyl)-1-propanol | $R_{20}$ = 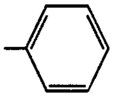<br>$R_{21}$ = 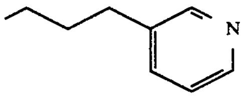 | 0.50 |

TABLE 10-continued

| No. | a) compound | b) aldehyde | c) amino alcohol | Structure<br>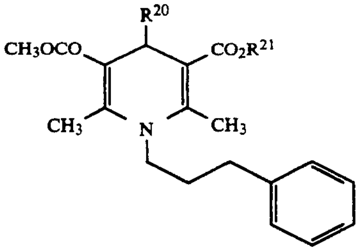 | $IC_{50}$ ng/ml |
|---|---|---|---|---|---|
| 57 | 1,4-dihydro-4-(3-nitrophenyl)-2,6-dimethyl-1-(3-phenylpropyl)-3,5-pyridinedicarboxylic acid 3-methyl-5-[3-(4-methylpiperazino)propyl]ester | 3-nitrobenzaldehyde | 1-(3-hydroxypropyl)-4-methylpiperazine | 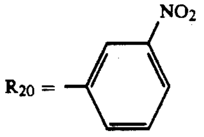<br>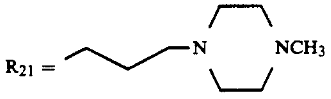 | 0.40 |
| 58 | 1,4-dihydro-4-(3-nitrophenyl)-2,6-dimethyl-1-(3-phenylpropyl)-3,5-pyridinedicarboxylic acid 3-methyl-5-[3-(3-pyridyl)propyl]ester | 3-nitrobenzaldehyde | 3-(3-pyridyl)-1-propanol | 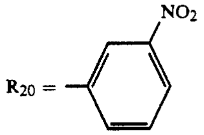<br>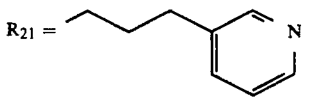 | 0.70 |

EXAMPLE 59

Preparation of (+)-1,4-dihydro -4-(3,4 -dimethoxyphenyl)-2,6-dimethyl-1-(3-phenylpropyl)-3,5-pyridinedicarboxylic acid 3 -methyl-5-[3-(3-pyridyl)propyl]ester a) Optical resolution of racemic 1,4-dihydro-4-(3,4-dimethoxyphenyl)-2-6-dimethyl-1-(3-phenylpropyl)-3,5-pyridinedicarboxylic acid 3-methyl ester 72.5 g (0.156 mol) of racemic 1,4-dihydro-4-(3,4-dimethoxyphenyl)-2-6-dimethyl-1-(3-phenylpropyl)-3,5-pyridinedicarboxylic acid 3-methyl ester prepared in Example 1 and 45.9 g (0.156 mol) of (−) cinchonidine were dissolved in 650 ml of methanol at 55° C. and the solution was cooled to room temperature. Insoluble substance was filtered off and methanol was removed under reduced pressure. The residue was dissolved in 1000 ml of ethyl acetate at 55° C. and 800 ml of n-hexane was added slowly to the solution. After cooling to room temperature the solution was allowed to stand overnight and the resultant crystals were collected by filtration. The crystals were then dissolved in 400 ml of chloroform and the solution was washed with 400 ml of 1N HCl to remove cinchonidine. The organic layer was concentrated to dryness in vacuo to get 21.0 g of (+)-1,4-dihydro-4-(3,4-dimethoxyphenyl)-2-6-dimethyl-1-(3-phenylpropyl)-3,5-pyridinedicarboxylic acid 3-methyl ester. $[\alpha]_D$(15° C.)=35.9(EtOH 1.3%).

The filtrate from the first crystallization was concentrated in vacuo and the residue was dissolved in 400 ml of chloroform. The solution was washed with 400 ml of 2N HCl and concentrated in vacuo. Resultant residue was dissolved in 120 ml of chloroform and 270 ml of *n*-hexane at 55° C. and the solution was allowed to stand overnight at room temperature. The crystals thus formed were filtered off and the filtrate was concentrated to dryness to get 22.75 g of (−)-1,4-dihydro-4-(3,4-dimethoxyphenyl)-2,6-dimethyl-1-(3-phenylpropyl)-3,5-pyridinedicarboxylic acid 3-methyl ester. $[\alpha]_D$(15° C.)=−35.5 (EtOH 1.2%)

Optical purity of the above compounds was determined by HPLC using Sumichiral OA2000 (4mm ID×250 mm, Sumitomo Chemicals, Osaka) at a flow rate of 1 ml/min with 2.5 mM ammonium acetate in methanol. The optical purity of (+) and (−) form of the carboxylic acid estimated from the peak area was proved to be more than 95%.

b) Preparation of (+) -1,4-dihydro -4-(3,4-dimethoxyphenyl)-2-6-dimethyl-1-(3-phenylpropyl-3,5-pyridinedicarboxylic acid 3-methyl-5 -[3-(3-pyridyl)propyl]ester To a solution of 465 mg (1 mmol) of (+)-1,4-dihydro-4-(3,4-dimethoxyphenyl)-2,6-dimethyl-1-(3-phenylpropyl)-3,5-pyridinedicarboxylic acid 3-methyl ester (prepared in Example 59a) in 2.5 ml of dichloromethane 399 mg (3 mmol) of 3-(3-pyridyl)propanol and 306 mg (1.2 mmol) of 2-chloro-1-methylpyridinium iodide is added. After stirring at room temperature for 4 hours the solvent was distilled off under reduced pressure and 20 ml of saturated aqueous sodium chloride was added to the residue. The product was extracted 3 times with 20 ml of ethyl acetate and the extract was dried over anhydrous sodium sulfate and concentrated in vacuo. The residue was purified by silica gel chromatography (ethyl acetate: n-hexane=2:1) to get 348 mg of (+)-1,4-dihydro-4-(3,4-dimethoxyphenyl)-2,6-dimethyl-1-(3-phenylpropyl)-3,5-pyridinedicarboxylic acid 3-methyl-5-[3-(3-pyridyl)propyl] ester in 60% yield.

$^1H$ NMR ($CDCl_3$): 8.39 (2H, m) 7.35 (1H, d, J=9.3) 7.12–7.28 (4H, m) 7.01 (2H, d, J=8.1) 6.79 (1H, s) 6.68 (2H, s) 5.14 (1H, s) 4.05–4.12 (2H, m) 3.73 (3H, s) 3.72 (3H, s) 3.70 (3H, s) 3.61 (2H, t, J=8.1) 2.58 (2H, t, J=8.1) 2.40–2.53 (2H, m) 2.43 (3H, s) 2.37 (3H, s) 1.88–1.99 (2H, m).

MS m/z 584($M^+$).

EXAMPLE 60

Preparation of (−)-1,4 -dihydro-4 -(3,4-dimethoxyphenyl)-2,6-dimethyl-1-(3-phenyl-propyl)-(3,5-pyridinedicarboxylic acid 3-methyl-5-[3 -(3-pyridyl)propyl]ester To a solution of 465 mg (1 mmol) of (−)-1,4-dihydro-4-(3,4-dimethoxyphenyl)-2-6-dimethyl-1-(3-phenyl-propyl)- 3,5-pyridinedicarboxylic acid 3-methylester prepared in Example 59a) in 2.5 ml of dichloromethane 399 mg (3 mmol) of 3-(3-pyridyl)propanol and 306 mg (1.2 mmol) of 2-chloro-1-methylpyridinium iodide was added. After stirring at room temperature for 4 hours the solvent was distilled off under reduced pressure and 20 ml of saturated aqueous sodium chloride was added to the residue. The product was extracted 3 times with 20 ml of ethyl acetate and concentrated in vacuo. The residue was purified by silica gel chromatography (ethyl acetate n-hexane=2:1) to get 378 mg of (−)-1,4-dihydro-4-(3,4-dimethoxyphenyl)-2,6-dimethyl-1-(3-phenylpropyl)-3,5-pyridinedicarboxylic acid 3-methyl-5-[3-(3-pyridyl)propyl]ester in 65% yield.

EXAMPLE 61

Preparation of (+)-1,4-dihydro -4 -(3,4-dimethoxyphenyl)-2,6-dimethyl-1-(3-phenyl-propyl)-3,5-pyridinedicarboxylic acid 3-methyl-5-[3-(3-pyridyl)propyl]ester hydrochloride 6.0 ml of 0.4N HCl in methanol was added to an ice-cooled methanol solution (10 ml) of 1.17 g(2.0 mmol) of (+)-1,4-dihydro-4-(3,4-dimethoxyphenyl)-2,6-dimethyl-1-(3-phenylpropyl)-3,5-pyridinedicarboxylic acid 3-methyl-5-[3-(3-pyridyl)propyl]ester. After evaporation of methanol the residue was washed twice with ice-cooled ether and dried in vacuo. The residue was dissolved in 25 ml of water and the solution was lyophilised to give 1.18 g of (+)-1,4-dihydro-4-(3,4-dimethoxyphenyl)-2,6-dimethyl-1-(3-phenylpropyl)-3,5-pyridinedicarboxylic acid 3-methyl-5-[3-(3-pyridyl)-propyl] ester hydrochloride. $[\alpha]_D(15^\circ C.)=4.2$(EtOH 1.1%).

EXAMPLE 62

Preparation of (−) -1,4-dihydro-4-(3,4 -dimethoxyphenyl)-2,6-dimethyl-1-(3-phenylpropyl)-3,5-pyridinedicarboxylic acid 3-methyl-5-[3-(3-pyridyl)propyl]ester hydrochloride 6.0 ml of 0.4N HCl in methanol was added to an ice-cooled methanol solution (10 ml) of 1.17 g (2.0 mmol) of (+)-1,4-dihydro-4-(3,4-dimethoxyphenyl)-2-6-dimethyl-1-(3-phenylpropyl)-3,5-pyridinedicarboxylic acid 3-methyl-5-[3-(3-pyridyl)propyl]ester. After evaporation of methanol the residue was washed twice with ice-cooled ether and dried in vacuo. The residue was dissolved in 25 ml of water and the solution was lyophilised to give 1.10 g of (−)-1,4-dihydro-4-(3,4-dimethoxyphenyl)-2,6-dimethyl-1-(3-phenylpropyl-3,5-pyridinedicarboxylic acid 3-methyl-5-[3-(3-pyridyl)-propyl]ester hydrochloride. $[\alpha]_D(15^\circ C.)=-4.3$(EtOH 1.0%).

EXAMPLE 63

Test of effect on overcoming anti-cancer drug resistance

Vincristine-resistant mouse P388 leukemia cells were used as an example of resistant cancer cells. RPMI-1640 medium containing 5 μM of 2-mercaptoethanol and 10% fetal calf serum was used for incubation.

The cells were inoculated on a 96-well microplate in $1\times10^4$/50 μl/well and 25 μl each of vincristine solution having a specific concentration and an aqeous solution of the test compound (4 μg/ml) was added thereto. After culturing at 37° C. for 2 days, the viable cells were counted by the MTT method and a dose-response curve of vincristine was prepared. Based on the curve, the concentration ($IC_{50}$) of vincristine producing a 50% inhibition of growth was determined. The $IC_{50}$ in the presence of each compound is shown in Tables 1 to 10. In the case of vincristine alone, the $IC_{50}$ was 50 to 100 ng/ml, whereas where the test compound was present in a concentration of 1 μg/ml, the $IC_{50}$ varied between 0.15 and 15 ng/ml, indicating that the compounds had a remarkable effect in reducing the cells' resistance to vincristine.

EXAMPLE 64

Test of Enhancement of Therapeutic Effect in Mice with Vincristine-resistant P388 Leukemia Vincristine-resistant P388 leukemia cells ($1\times10^6$) were intraperitoneally transplanted to $CDF_1$ mice, five mice being grouped in one group. A particular amount of the test compound and 100 μg/kg of vincristine were intraperitoneally administered to determine the number of days for which the mice remained alive.

The tested compounds were mixed with polyvinyl-pyrrolidone to make a 1:4 mixture by dissolving them in dichloromethane followed by evaporation and the mixture was dissolved in saline for injection.

The enhancement of therapeutic effect is expressed by a ratio of T/V (%), namely, a ratio of the increased life span when vincristine and the test compound were administered in combination to the increased life span when vincristine alone was used. T/V is shown in Table 11.

The effects of verapamil, a calcium channel blocker, and of 1,4-dihydro-4-(3,4-dimethoxyphenyl)-2,6-dimethyl-1-(3-benzyloxypropyl)-3,5-pyridinedicarboxylic acid 3,5-dimethyl ester were also tested in the same way and the results are shown in Table 11.

These results revealed that the compounds prepared in the Examples were effective in prolonging the life of tumor bearing mice when used in combination with the antitumor drug vincristine. They were more effective than either verapamil or 1,4-dihydro-4-(3,4-dimethoxyphenyl)-2,6-dimethyl-1-(3-benzyloxypropyl)-3,5-pyridinedicarboxylic acid 3,5-dimethyl ester which is claimed in JP No. 01-316357.

TABLE 11

| compound | dose (mg/kg) | schedule times/day × days | T/V (%) |
|---|---|---|---|
| Verapamil | 70 | 1 × 5 | 125 |
| Verapamil | 70 | 2 × 5 | 128 |

TABLE 11-continued

| compound | dose (mg/kg) | schedule times/day × days | T/V (%) |
|---|---|---|---|
| Example No. | | | |
| 1 | 50 | 2 × 5 | 114 |
| 1 | 75 | 2 × 5 | 106 |
| 7 | 50 | 1 × 5 | 126 |
| 7 | 100 | 1 × 5 | 144 |
| 8 | 100 | 2 × 5 | 120 |
| 8 | 100 | 1 × 10 | 121 |
| 8 | 200 | 1 × 10 | 145 |
| 10 | 100 | 1 × 10 | 105 |
| 10 | 100 | 2 × 5 | 128 |
| 19 | 50 | 1 × 5 | 115 |
| 19 | 100 | 1 × 5 | 126 |
| 19 | 200 | 1 × 5 | 133 |
| 28 | 50 | 1 × 5 | 120 |
| 47 | 50 | 1 × 5 | 128 |
| 47 | 100 | 1 × 5 | 144 |
| a) | 50 | 1 × 5 | 107 |
| a) | 100 | 1 × 5 | 104 |

a) 1,4-dihydro-4-(3,4-dimethoxyphenyl)-2,6-dimethyl-1-(3-benzyloxypropyl)-3,5-pyridinedicarboxylic acid 3,5-dimethylester

EXAMPLE 65

Effect of (+) and (−) -1,4-dihydro-4 -(3,4-dimethoxyphenyl)-2-6-dimethyl-1-(3-phenylpropyl)-3,5-pyridinedicarboxylic acid 3-methyl-5-[3-(3-pyridyl)propyl]ester hydrochloride on regression of tumor in colon 26 bearing mice 20 mg of colon 26 cells were transplanted subcutaneously to CDF1 mice (6 weeks old, female) on day 0. On day 6 the diameter of the tumor was measured and groups of 5 mice were selected having equal average tumor size. On day 7 and 14, 10 mg/kg of adriamycin was injected i.v. and the tested compounds were administered p.o. at 0, 8, 24, 32 hours after the injection of adriamycin. Adriamycin was dissolved in saline to a concentration of 2 mg/ml and the compounds in Example 61 and 62 were dissolved in saline to a concentration of 50 mg/ml. The diameter of the tumor was measured each week and tumor weight was estimated as follows:

$$\text{tumor weight (g)} = \frac{L \times S^2}{2000}$$

(L:long diameter, S:short diameter, mm)

The results shown in Table 12 indicate that the compounds in Examples 61 and 62 are effective in reducing tumor weight in combination with adriamycin.

TABLE 12

| Experiment No. | Example No. | Adriamycin (mg) | dose (mg) | tumor weight (g) |
|---|---|---|---|---|
| 1) | No. 61 | 10 | 250 | 2.2 |
| 2) | No. 61 | 10 | 500 | 2 |
| 3) | No. 62 | 10 | 250 | 1.8 |
| 4) | No. 62 | 10 | 500 | 1.1 |
| 5) | — | 10 | — | 2.7 |
| 6) | — | 0 | — | 4.5 |

We claim:

1. A 1,4-dihydropyridine derivative of Formula 1 or a pharmaceutically acceptable salt thereof:

Formula 1

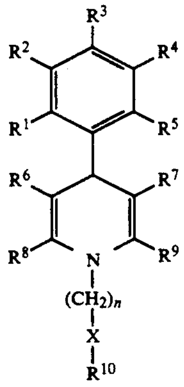

wherein each of $R^1$, $R^2$, $R^3$, $R^4$ and $R^5$ independently represents a hydrogen atom, a lower alkyl group having 1 to 3 carbon atoms, a hydroxy group, a lower alkyloxy group having 1 to 3 carbon atoms, or a nitro group, or two of the substituents represented by $R^1$, $R^2$, $R^3$, $R^4$ and $R^5$ adjacent to each other on the benzene ring are combined together to form an alkylenedioxy group having 1 to 3 carbon atoms;

at least one of $R^6$ and $R^7$ represents:

(i) an alkyloxycarbonyl group selected from the group consisting of a pyridylalkyloxycarbonyl group which may be substituted on the pyridyl moiety, a N,N-dialkylaminoalkyloxycarbonyl group in which the dialkylamino moiety may take on a cyclic structure, a N,N-alkylarylaminoalkyloxycarbonyl group, a N,N-diaralkylaminoalkyloxycarbonyl group, and a N,N-aralkylalkylamino-alkyloxycarbonyl group; or (ii) an alkylaminocarbonyl group selected from the group consisting of a pyridylalkylaminocarbonyl group which may be substituted on the pyridyl moiety, a (N,N-dialkylamino)alkylaminocarbonyl group in which the dialkylamino moiety may take on a cyclic structure, a (N,N-alkylarylamino)alkylaminocarbonyl group, a (N,N-diaralkylamino)alkylaminocarbonyl group, and a (N,N-aralkylalakylamino)alkylaminocarbonyl group;

and where when only only one of $R^6$ and $R^7$ represents said alkyloxycarbonyl group or said alkylaminocarbonyl group, the other is an unsubstituted alkyloxycarbonyl group;

each of $R^8$ and $R^9$ independently represents a hydrogen atom or a lower alkyl group having 1 to 5 carbon atoms;

n represents an integer of 2 to 9;

X represents a methylene group or oxygen atom, wherein the methylene is optionally substituted with a lower alkyl group having 1 to 5 carbon atoms, or a lower alkyloxy group having 1 to 5 carbon atoms; and, $R^{10}$ represents an aryl group or an aralkyl group, wherein the aryl moiety in the aryl group and aralkyl group is phenyl or naphthyl at said aryl moiety and is optionally substituted with a substituent selected from the group consisting of a halogen atom, a lower alkyl group having 1 to 5 carbon atoms, a lower alkyloxy group having 1 to 5 carbon atoms, a hydroxy group an aryl group, an aryloxy group, an aralkyl group, or an aralkyloxy group, or two substituents adjacent to each other on the benzene ring are combined together to form an alkylenedioxy group having 1 to 3 carbon atoms.

2. The 1,4-dihydropyridine derivative or salt according to claim 1, wherein at least one of $R^6$ and $R^7$ is a group of Formula 2:

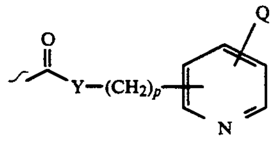

Formula 2 wherein

Y represents an oxygen atom or NH; Q represents a hydrogen atom, a halogen atom, an alkyl group, an aryl group, an aralkyl group, a lower alkyloxy group having 1 to 5 carbon atoms; and p represents an integer of from 1 to 4.

3. The 1,4-dihydropyridine derivative or salt according to claim 1, wherein at least one of $R^6$ and $R^7$ is a group of Formula 3:

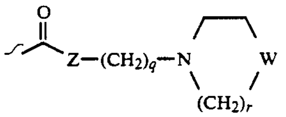

Formula 3 wherein

Z represents an oxygen atom or NH; W represents a methylene group, nitrogen atom, or oxygen atom, wherein the methylene is optionally substituted with an alkyl group having 1 to 5 carbon atoms, an aryl group, an aralkyl group or carbonyl group, and the nitrogen atom is optionally substituted with an alkyl group having 1 to 5 carbon atoms, an aryl group, an aralkyl group or carbonyl group; and q represents an integer of 1 to 4; and r represents an integer of 1 to 3.

4. The 1,4-dihydropyridine derivative or salt according to claim 2, wherein Y is an oxygen atom; Q is a hydrogen atom; and p is 3.

5. The 1,4-dihydropyridine derivative or salt according to claim 3, wherein Z is an oxygen atom.

6. The 1,4-dihydropyridine derivative or salt according to claim 3, wherein Z is an oxygen atom; W represents a nitrogen atom substituted with an alkyl group having 1 to 5 carbon atoms, an aryl group, an aralkyl group or carbonyl group; and q represents an integer of 2 to 4; and r represents an integer of 1 to 2.

7. The 1,4-dihydropyridine derivative or salt according to claim 1, wherein said derivative is 1,4-dihydro-4-(3,4-dimethoxyphenyl)-2,6-dimethyl-1-(3-phenylpropyl)-3,5-pyridinedicarboxylic acid 3-methyl-5-[3-(3-pyridyl)propyl]ester represented by the following Formula 4:

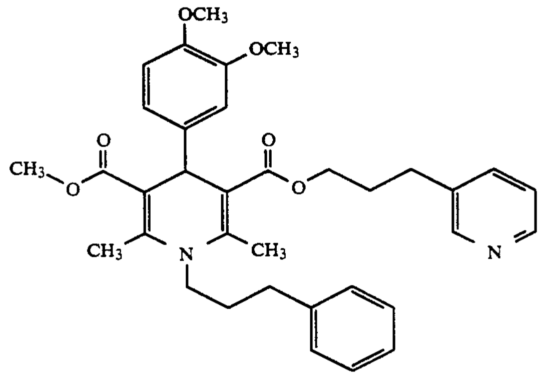

8. The 1,4-dihydropyridine derivative or salt according to claim 1 which is optically active.

9. A method of treatment of a human or animal patient to prevent or reduce acquired resistance to cancer treatment agents comprising administering an effective amount of a compound of claim 1 optionally in combination with an effective amount of a cancer treatment agent.

* * * * *